(12) United States Patent
Wilkins

(10) Patent No.: US 6,207,406 B1
(45) Date of Patent: Mar. 27, 2001

(54) MICROBIAL SAMPLING APPARATUS AND PROCESS

(76) Inventor: Judd R. Wilkins, 281 Littletown Quarter, Williamsburg, VA (US) 23185

( * ) Notice: Subject to any disclaimer, the term of this patent is extended or adjusted under 35 U.S.C. 154(b) by 0 days.

(21) Appl. No.: 09/418,912

(22) Filed: Oct. 15, 1999

(51) Int. Cl.[7] .................................................. C12Q 1/24
(52) U.S. Cl. ......................................... 435/30; 435/309.1
(58) Field of Search ............................. 435/287.1, 287.7, 435/288.3, 305.1, 309.1, 309.4, 30; 422/102

(56) References Cited

U.S. PATENT DOCUMENTS

| | | |
|---|---|---|
| 3,066,342 | 12/1962 | Jackson . |
| 3,074,276 | 1/1963 | Moos . |
| 4,717,667 * | 1/1988 | Provonchee .......................... 435/292 |
| 4,848,165 | 7/1989 | Bartilson ............................ 73/864.71 |
| 4,848,167 | 7/1989 | Gordon .............................. 73/864.71 |
| 5,063,026 | 11/1991 | Wong ................................... 422/102 |
| 5,243,865 | 9/1993 | Hsu .................................. 73/864.72 |
| 5,373,748 | 12/1994 | Lioy ................................. 73/864.71 |
| 5,554,537 | 9/1996 | Sharp ................................ 435/309.1 |
| 5,695,988 * | 12/1997 | Chong ............................... 435/305.1 |

* cited by examiner

*Primary Examiner*—David A. Redding
(74) *Attorney, Agent, or Firm*—Wallace J. Nelson

(57) ABSTRACT

A sampling apparatus and process for obtaining microbial samples from a suspect surface, such as a meat processing facility, animal carcass, and the like, wherein a agar saturated porous plastic foam strip is placed in contact with the suspect surface and thereafter incubated to indicate the presence and quantity of microbial growth on the suspect surface. The porous plastic foam strip is attached to one surface of a double faced adhesive tape with the other tape face being adhesively attached to a spool on a hand roller to permit hand pressure application of the porous plastic sampler to the test surface. For use of the sampler without the roller, one surface of the double face adhesive tape is attached to a plastic strip and the sampler may be hand positioned directly on the suspect test surface. Agar for specific known bacteria may be employed to saturate the porous plastic foam sampler.

8 Claims, 2 Drawing Sheets

US 6,207,406 B1

MICROBIAL SAMPLING APPARATUS AND PROCESS

FIELD OF THE INVENTION

This invention relates to a microbial sampling apparatus and process and relates specifically to a contact device for screening surfaces for microbial contamination in the food and similar industries.

BACKGROUND OF THE INVENTION

Recently, numerous outbreaks of food poisoning have resulted from consuming ground beef contaminated with toxigenic strains of *Escherichia coli* or chickens infected with shigella or salmonella. These outbreaks have become a major public health problem and a large-scale industry and government program is underway to minimize and prevent further attacks of food poisoning. One aspect of this program involves examination of the sanitary practices in food processing facilities, especially meat and poultry processing plants. Inherent in such a program is a determination of the microbial profile or burden in work stations, carcasses, and any surface coming in contact with the product that could be a source of contamination.

Current surface sampling techniques include rubbing a sterile moist cotton swab or moist pieces of gauze across a suspect surface, and in the laboratory after elution, the number and types of microorganisms are determined. Another technique uses nutrient agar molded in the shape of a "sausage". A section or slice of this sausage agar is taken and the sliced section pressed down on the suspect surface, removed, and after incubation, the numbers and types of microorganisms determined. The present invention utilizes the advantages of these systems while minimizing the disadvantages thereof.

It is accordingly, an object of the present invention to provide an improved method for sampling of surfaces for suspect microorganisms.

Another object of the present invention is to provide a novel sampling tool for determining microorganism presence, identification, and quantity on a test surface.

It is another object of the present invention to employ double-faced adhesive tape for attaching an agar saturated porous plastic foam to a support base to form a microorganism sampling tool.

Another object of the present invention is a process of making a microorganism sampling and identification tool.

SUMMARY OF THE INVENTION

According to the present invention, the foregoing and additional objects are attained in the preferred embodiment of the invention by using porous plastic foam for absorbing melted, and subsequently gelled, nutrient agar to form a block and attaching a support surface to one surface of the porous plastic foam to permit positioning of the other agar surface onto a test suspect microorganism-contaminated surface. The support surface is a double-faced adhesive tape with one face of the tape adhered to the plastic foam and the other face adhered to a roller rotatably attached to a handle for rotatable support.

A test surface, animal carcass, processing table or the like, is sampled by rolling the roller over the test surface. Microorganisms are recovered from the test surface(s) by the combined natural sticky action of agar and the bristle-like action of the plastic foam. After sampling the roller spool may be removed from the handle and the entire roller, or at least the agar saturated plastic foam, is placed in an incubator in a conventional manner to facilitate microorganism growth and to give an indication of the numbers and types of recovered microorganisms by conventional biochemical and other techniques.

BRIEF DESCRIPTION OF THE DRAWINGS

A more complete appreciation of the invention and many of the attendant advantages thereof will be more readily apparent as the same becomes better understood with reference to the accompanying drawings wherein.

DETAILED DESCRIPTION

Figure 1:
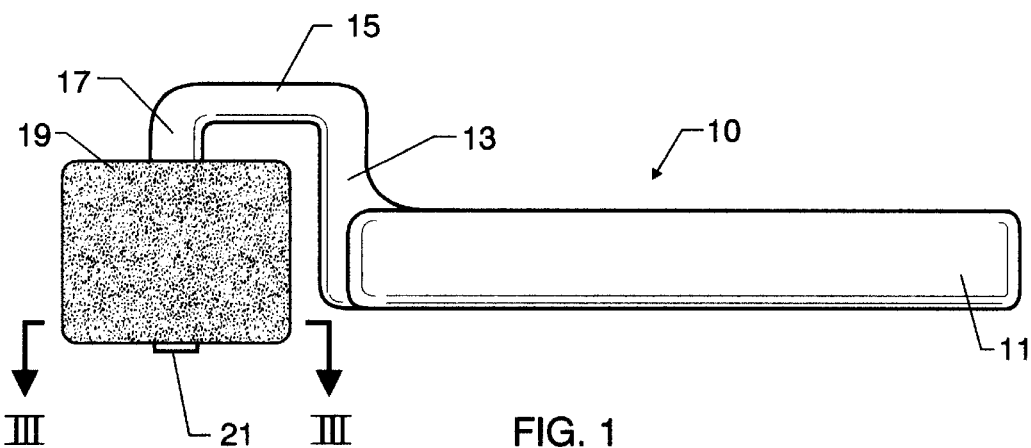
FIG. 1 is a schematic side view of a hand operated microbial sampling tool according to the present invention.
Figure 2:
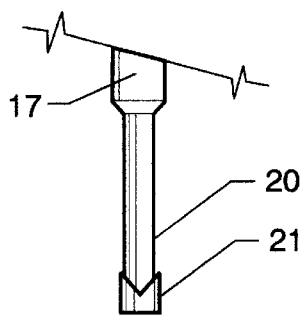
FIG. 2 is a schematic representation of the spindle portion of the tool shown in FIG. 1.

Referring now to the drawings and more particularly to FIG. 1, the preferred embodiment of the sampling tool of the present invention is shown and designated generally by reference numeral 10. Sampling tool includes an elongated hand-manipulable handle 11 terminating at one end with a U-shaped extension having a first leg 13 perpendicularly disposed relative to the longitudinal axis of handle 11 and is integrally attached at a first end thereof to handle 11. A second leg 15 of U-shaped extension is attached perpendicularly disposed relative to the first leg 13 of the U-shaped extension. The third leg 17 of the U-shaped handle extension is integrally attached at a first end thereof to second leg 15 and is parallel with first leg 13. Third leg 17 is provided with a reduced diameter segment 20 (FIG. 2) at the second end thereof and serves as a spindle for a rotatable spool 19. A latch/plug 21 on the reduced diameter segment 20 of third leg 17 serves to secure spool 19 in rotating relationship therewith in a conventional manner.

Figure 3:
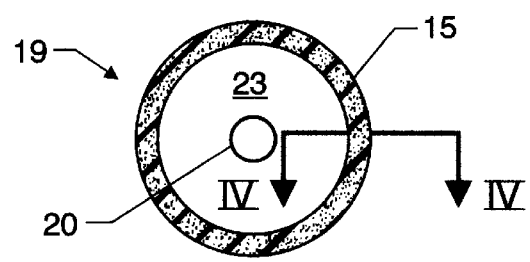
FIG. 3 is a schematic sectional view of the roller mechanism of the tool shown in FIG. 1 and taken along line III—III thereof.
Figure 4:
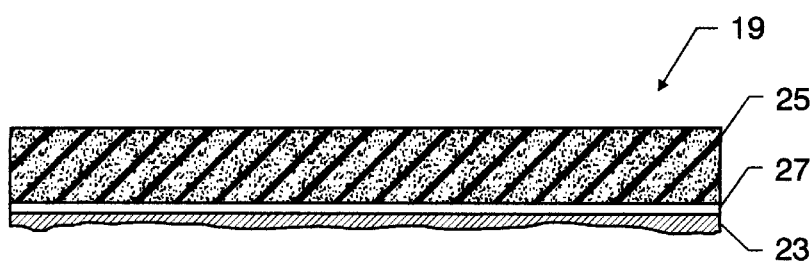
FIG. 4 is a sectional view of the sampling tool as taken along line IV—IV of FIG. 3.

Referring now more particularly to FIG. 3, spool 19 includes a cylindrical section 23 rotatably disposed on spindle 20. A layer of plastic foam 25 covers the exterior of spool 19. Plastic foam layer 25 is secured to spool 19 by a double faced adhesive tape 27 (FIG. 4). One surface of adhesive tape 27 is adhered to one surface of plastic foam layer 25 with the other adhesive face of tape 27 being adhered to cylindrical section 23 of spool 19.

Figure 5:
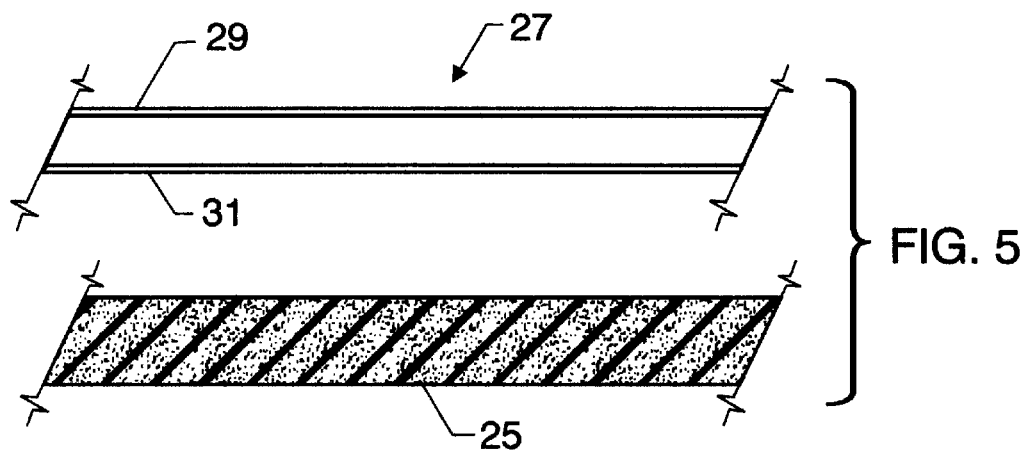
FIG. 5 is an exploded view of two of the component parts employed in construction of the tool shown in FIG. 1.

Referring more particularly to FIG. 5, raw materials plastic foam 25 and double faced tape 27 are shown. As illustrated, one of the adhesive faces of tape 27 is exposed as one paper backing strip is peeled away when the length of tape employed is removed from a roll of the tape. The other adhesive surface of tape 31 remains covered by a backing strip of heavy duty paper. Prior to use in the present invention, this paper backing strip is replaced by a plastic sheet backing strip 29, as will be further explained hereinafter.

Figure 6:
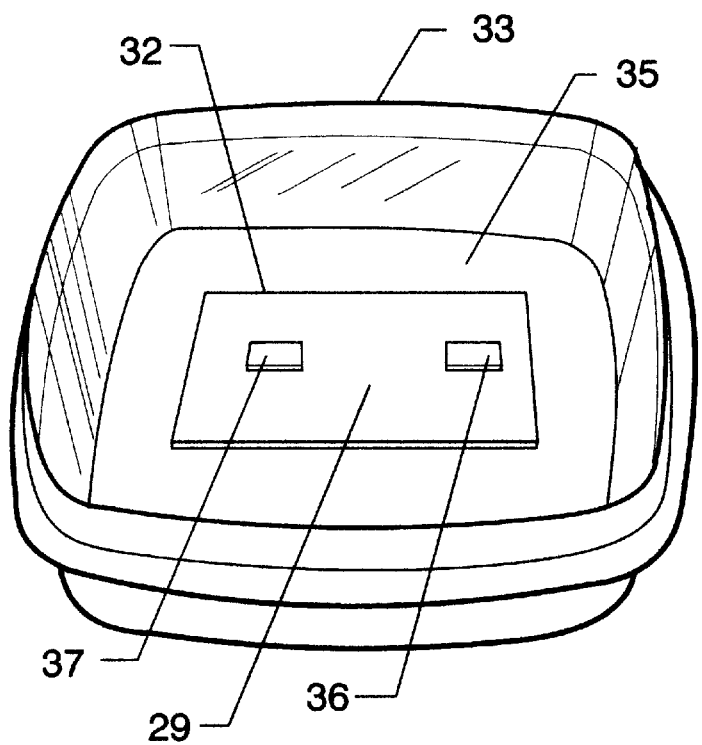
FIG. 6 is a schematic view of the materials employed in the processing of the components shown in FIG. 5 for use in the preparation of the tool of FIG. 1.

Referring now more particularly to FIG. 6, tape 27 and plastic foam layer 25 are connected together by placing the exposed adhesive surface 31 in contact with plastic foam layer 25. This combined structure 32 is then placed in a vessel 33 containing a quantity of melted agar 35 of sufficient depth to immerse the layer of plastic foam layer 25. A pair of weights 35,36 are positioned on the protected surface of tape 27 to maintain the plastic foam layer 25 immersed in agar 35. The entire vessel is then placed in a refrigerator for approximately thirty minutes to cause jelling or solidification of the agar. After agar solidification, the weights are removed and additional agar added to cover the tape/plastic foam and the refrigeration procedure repeated. The sampler assembly 32 is then removed from vessel 33 and excess agar trimmed away. The protective cover is then removed from tape 27 and the assembly is adhesively secured to a plastic strip 29.

In a specific embodiment, the components of the sampler of the present invention include a double-faced adhesive tape 27 and porous plastic foam 25 (FIG. 5). Double-faced fiberglass cloth adhesive tape manufactured by Manco, Inc. is readily available from hardware stores as "Cloth Carpet Tape" in widths of one and one-half inches and lengths of twelve to twenty feet. The tape is covered with heavy duty paper that is removable to expose the adhesive faces. A one and one-half inch by three and one-half inch piece of the tape is pressed to one side of a like size plastic strip after one paper liner is removed during unrolling of the tape. The plastic strips employed were cut from Gladware plastic food storage containers available from grocery stores. A similar size, one and one-half by three and one-half inch, piece of one-fourth inch thick porous plastic foam was firmly pressed onto the remaining exposed side of the adhesive tape. Polystyrene porous plastic foam is available from craft stores such as Ben Franklin Crafts in Yorktown, Va. and is available in two foot widths and thickness of one fourth, one half, one inch and two inches. The composite sampler (tape and foam) was placed in a 4×4 inch sandwich sized plastic container 33 (FIG. 6) and anchored with two weights (hexagonal nuts) to prevent drifting in the agar solution.

In a plastic measuring cup, two teaspoons of agar was added to two hundred milliliters of water (about 1.0 percent) and placed in a microwave oven at a high setting for five minutes to dissolve the agar. The agar employed in this specific example was obtained from Difco Laboratories, Detroit, Mich. Two drops of food coloring were added to the melted agar for illustrative purposes. Sufficient agar was added to vessel 33 to cover the foam layer of the sampler (FIG. 6) and the vessel placed in a refrigerator for thirty minutes. The weights were then removed and additional melted agar added to barely cover the sampler surface. After another thirty minutes in the refrigerator, the sampler was removed and excess agar trimmed from the edges of the sampler. The recovered sampler can then be employed as a surface sampler directly.

In order to adapt the sampler to a roller (FIG. 1) one of the paper protective cover for the adhesive tape is not removed. In this scenario, after 24 to 36 hours at ambient conditions, the paper liner was sufficiently dry to permit attachment to the roller with the duo-adhesive tape. However, the dried paper base was not firm or stable enough for surface sampling which required the plastic strip base.

In operation, the roller assembly shown in FIG. 1 is employed to sample a suspect test surface, (work station, animal carcass, or the like) and the complete spool assembly removed and incubated in a suitable laboratory to detect the presence and quantity of microorganisms taken from the surface, in a conventional manner.

Different agar preparations may be employed that are specific for a specific bacteria or groups of bacteria For example, to isolate *Eschericia coli*, Levine's E.M.B. agar or Endo agar would be used and S.S. agar or MacConkey's agar would be used for the isolation of shigella and salmonella. Also, the specific examples sizes given herein are to be considered as exemplary and not exhaustive. In this respect, the adhesive-plastic foam combination sampler could be readily adapted to a larger roller device for ease of covering a wide sampling area. Additionally, the size and shape of the samplers could be designed for unusual or difficult sampling area. In all cases the samplers (either the entire roller unit, or the adhesive foam portion removed from the roller), would be returned under sterile conditions to a laboratory and, after incubation, the numbers and types of recovered microorganisms determined by conventional biochemical and other techniques.

Thus, although the invention has been described by specific embodiments thereof, it is not so limited, and there are numerous variations and modifications thereof that will be readily apparent to those skilled in the art in the light of the above teachings. It is therefore to be understood that, within the scope of the appended claims, the invention may be practiced other than as specifically described herein.

What is claimed as new and desired to be secured by Letters Patent is:

1. Apparatus for collecting a microbial sample from a suspect surface comprising:

a sheet of porous plastic foam having a first and a second planar surface;

a microbial growth media contained within and exposed on said first surface of said sheet of porous plastic foam;

means for releasably positioning said sheet of porous plastic foam into contact with a surface to be sampled for microbial contamination;

said means for releasably positioning said sheet of porous plastic foam including a double faced adhesive tape having a first adhesive surface contacting said second planar surface of said sheet of porous plastic foam and a second adhesive surface attached to a support.

2. The apparatus of claim 1 wherein said support attached to said second adhesive surface is a plastic strip of material that permits hand pressure to be applied to said sheet of porous plastic foam to said surface to be sampled.

3. The apparatus of claim 1 wherein said support attached to said second adhesive surface is a cylindrical roller and said second adhesive surface is in adhesive contact with and completely encircles said cylindrical roller.

4. The apparatus of claim 3 including means rotatably connecting said cylindrical roller to a hand manipulatable handle.

5. The apparatus of claim 4 wherein said cylindrical roller is a spool having a transverse opening extending therethrough and a spindle extending from said hand manipulatable handle and received said transverse opening of said spool.

6. The apparatus of claim 5 including a latch disposed on said spindle and serving to releasably connect said spool to said hand manipulatable handle.

7. A method of preparing a microbial sampler comprising the steps of:

(a) providing a sheet of porous plastic foam;

(b) providing a roll of double face adhesive tape having a heavy duty paper backing protecting each adhesive face of the tape;

(c) removing a length of the double face adhesive from the roll such that an exposed adhesive tape face is obtained by peeling away the protective paper backing from one face of the adhesive tape;

(d) adhesively securing the exposed adhesive face to the sheet of porous plastic foam;

(e) employing a strip of plastic material to replace the remaining protective paper backing on the remaining adhesive face of the adhesive tape;

(f) providing a container having a quantity of melted nutrient agar therein;

(g) immersing the sheet of porous plastic foam into the melted agar leaving the attached adhesive tape exposed;

(h) adding a weight to the exposed adhesive tape to maintain the immersed position of, and prevent movement of, the porous plastic foam in the agar;

(i) refrigerating the container for a period of time sufficient to cause the melted agar to jell;

(j) removing the container from the refrigerating environment, removing the weight and adding additional agar to completely immerse the adhesive tape covering on the porous plastic foam;

(k) refrigerating the container again to jell the additional agar, (l) removing the container from the refrigerating environment and trimming the excess agar from the agar saturated porous plastic foam and adhesive tape protective cover to recover a sampler that may be placed directly onto a suspect surface to collect sample of any microbial contaminants thereon.

8. The method of claim 7 including the additional steps of removing the protective cover from the adhesive tape to expose an adhesive tape surface and adhesively securing this exposed surface to a roller element to permit roller contact of the agar saturated plastic foam with a suspect surface.

* * * * *